United States Patent [19]

Hata et al.

[11] Patent Number: 5,099,851
[45] Date of Patent: Mar. 31, 1992

[54] AUTOMATIC SPHYGMOMANOMETER

[75] Inventors: Hideo Hata, Fujimi; Takahiro Souma, Kanagawa, both of Japan

[73] Assignee: Terumo Kabushiki Kaisha, Tokyo, Japan

[21] Appl. No.: 465,244

[22] PCT Filed: Sep. 9, 1988

[86] PCT No.: PCT/JP88/00916
§ 371 Date: Mar. 14, 1990
§ 102(e) Date: Mar. 14, 1990

[87] PCT Pub. No.: WO89/02244
PCT Pub. Date: Mar. 23, 1989

[30] Foreign Application Priority Data

Sep. 14, 1987 [JP] Japan .................................. 62-228463

[51] Int. Cl.$^5$ .............................................. A61B 5/02
[52] U.S. Cl. ..................................... 128/672; 128/680; 128/677
[58] Field of Search ............... 181/230, 231, 252, 258; 128/672, 675, 677, 679, 680–683

[56] References Cited

U.S. PATENT DOCUMENTS

| | | | |
|---|---|---|---|
| 3,527,204 | 9/1970 | Lem | 128/680 |
| 3,905,353 | 9/1975 | Lichowsky | 128/677 |
| 4,299,305 | 10/1981 | Eriksson | 181/230 |
| 4,353,434 | 10/1982 | Norris | 181/258 |
| 4,417,587 | 11/1983 | Ichinomiya | 128/682 |
| 4,424,883 | 1/1984 | Musiani | 181/230 |
| 4,627,440 | 12/1986 | Ramsey et al. | |
| 4,832,039 | 5/1989 | Perry | 128/680 |

FOREIGN PATENT DOCUMENTS 2087238  5/1982  United Kingdom ............... 128/680

OTHER PUBLICATIONS

European Search Report completed 11/27/90 by Examiner P.H.E.V. Fontenay in The Hague, citing 5 references listed herein.

Primary Examiner—Kyle L. Howell
Assistant Examiner—Robert L. Nasser, Jr.
Attorney, Agent, or Firm—Staas & Halsey

[57] ABSTRACT

An automatic sphygomomanometer for recognizing blood pressure through detection of Korotkoff sound or cuff pulsating pressure, comprising an air noise removing filter including an air reservoir and a flow resistor connected in series between a pressurizing pump and a cuff. After rectifying the noise generated by the pressing pump, the air is provided, and the blood pressure measurement is made. Preferably, the automatic sphygmomanometer has a flow resistor which has a resistor element made of fibers or paper. A bypass passage bypassing the air noise removing filter, is so controlled that, when the cuff pressure is below a predetermined level, the air supplied from the pressurizing pump is introduced into the cuff through the bypass passage so as to rapidly raise the pressure. After a predetermined level is reached, the air form the pressurizing pump is charged into the cuff through the air noise removing filter.

16 Claims, 4 Drawing Sheets

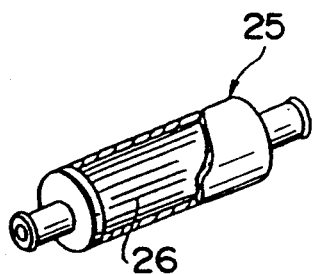
FIG. 5A
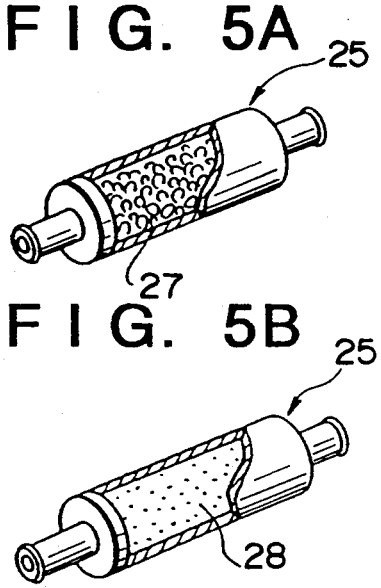
FIG. 5B
FIG. 5C
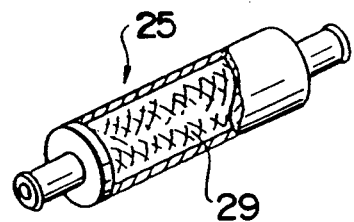
FIG. 5D
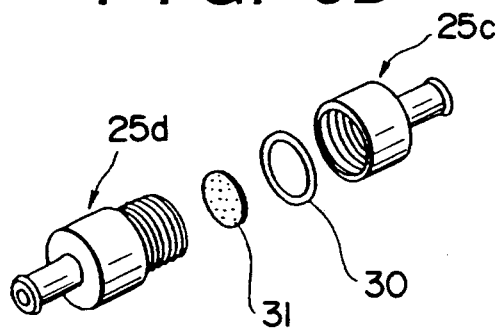
FIG. 5E
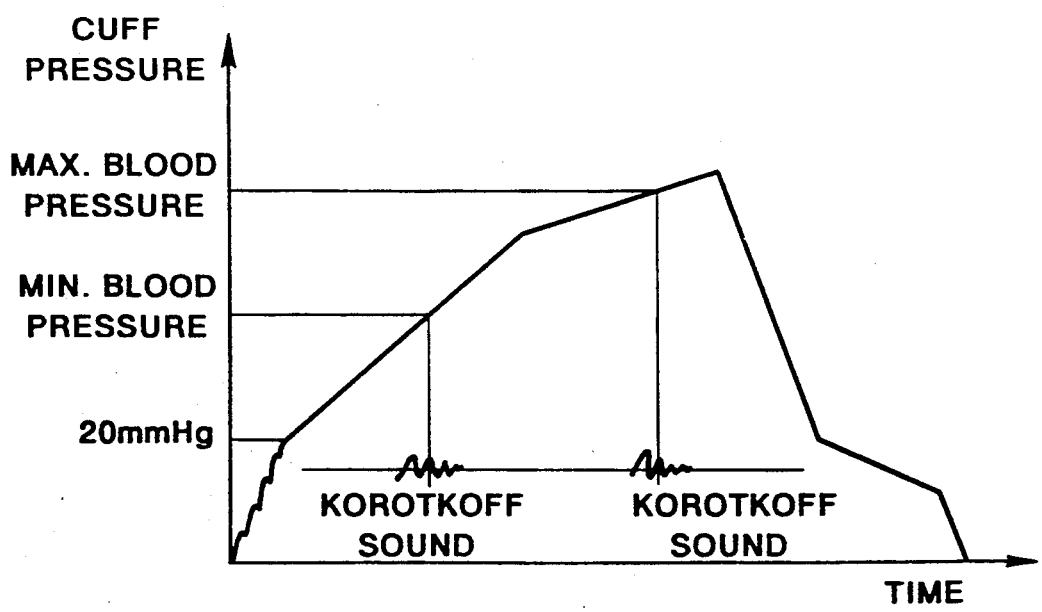
FIG. 6

AUTOMATIC SPHYGMOMANOMETER

TECHNICAL FIELD

This invention relates to an automatic sphygmomanometer having a pressurizing pump and, more particularly, to an automatic sphygmomanometer having an air noise removing device which is capable of removing noise produced by air supplied by the pressurizing pump, as well as to an automatic sphygmomanometer which is capable of raising cuff pressure in a short time.

BACKGROUND ART

Measurement of blood pressure by stethoscopic method employs the steps of raising the pneumatic pressure in a cuff to a predetermined level (maximum blood pressure plus α) and then progressively decreasing the pressure (at a rate of 2 to 4 mmHg per cardiac cycle).

If the measurement is conducted during rising of the pneumatic pressure instead of falling of the same, pulsation of the pressurizing pump and sounds generated by movable parts such as valves and the diaphragm of the pump are undesirably picked up by a microphone used for detecting Korotkoff sound or pressure sensor used for sensing pulsating pressure change in the cuff Thus, noises are undesirably input to the microphone or the pressure sensor Usually, the frequency bands of these noises overlap that of Korotkoff sound so that it is difficult to discriminate the Korotkoff sound from such noises Therefore, automatic sphygmomanometer, capable of measuring blood pressure during rise in the cuff pressure, is not popular insofar as a pressurizing means other than a compressed gas cylinder is used as the source of pressurized air.

Two methods are available for enabling a rise in the cuff pressure without noise: namely, (a) a method in which air supplied from a pressurizing pump is temporarily stored in an air reservoir and, after the pump is stopped, compressed air is released from the air reservoir into the cuff so as to establish a cuff pressure; and (b) a method in which air from the pressurizing pump is made to flow through a flow resistor so as to remove operation noise produced by the pump.

The first-mentioned method (a) has a disadvantage in that the size of the air reservoir must be increased which makes it difficult to install the reservoir on the sphygmomanometer, while the second-mentioned method (b) requires a pump having a large pumping capacity in order to overcome the resistance produced by the flow resistor. Both the methods (a) and (b) cannot establish the required cuff pressure in a short time. Namely, if the measurement is not conducted during the rise of the cuff pressure, it is permitted to supply air at high rate because noises produced during the air supply does not cause any problem. However, when the measurement is conducted during rise of the cuff pressure, the supply of air has to be conducted gently in such a manner as to avoid generation of noise. In addition, when the flow resistor is made of a single orifice, there is a risk that the diameter of the orifice port is progressively decreased or clogged with dust.

SUMMARY OF THE INVENTION

The present invention is aimed at obviating the abovedescribed problems of the prior art.

An object of the present invention is to provide an automatic sphygmomanometer in which the flow of air carrying pulsations generated by the pressurizing pump and sounds generated by valves and diaphragm is substantially rectified through an air noise removing filter so as to enable recognition of blood pressure during rise of the cuff pressure through detection of Korotkoff sound or cuff pulsating pressure, while ensuring degree of freedom of construction of the air noise removing filter.

Another object of the present invention is to provide an automatic sphygmomanometer in which a bypass passage of air is provided to bypass the air noise removing filter so that, when the cuff pressure is still below a predetermined level, air is supplied at high flow rate through the bypass passage so as to enable a prompt establishment of cuff pressure and, hence, quick recognition of the blood pressure.

To this end, according to the present invention, there is provided an automatic sphygmomanometer for determining blood pressure through detection of Korotkoff sound or cuff pulsating pressure, comprising: an air noise removing filter which includes an air reservoir and flow resistor connected in series between a pressurizing pump and the cuff; and a bypass valve connected in parallel to the air noise removing filter.

Preferably, the flow resistor has a flow resistor element made of fibers or a paper.

It is also preferred that the flow resistor has a flow resistor element containing bead-like spherical members.

It is also preferred that the flow resistor has a flow resistor element composed of a porous member.

It is also preferred that the flow resistor has a flow resistor element which includes a tube of a predetermined length.

Preferably, the tube is wound in a housing.

It is also preferred that the air reservoir is composed of a rigid tank.

It is also preferred that the air reservoir has an outer shell made of a soft material.

It is also preferred that the air reservoir is made of a bag and a frame which limits expansion of the bag in the thicknesswise direction.

According to another aspect of the present invention, there is provided an automatic sphygmomanometer for recognizing blood pressure through detection of Korotkoff sound or cuff pulsating pressure, comprising: an air noise removing filter which includes an air reservoir and a flow resistor connected in series between a pressurizing pump and the cuff; a bypass passage bypassing the air noise removing filter; and control means capable of performing control such that the air from the pressurizing pump is supplied to the cuff through the air noise removing filter when the cuff pressure is below a predetermined level.

In a preferred form, preferably, the control means includes a pressure sensor and executes the control in accordance with the pressure level sensed by the pressure sensor.

It is also preferred that the switching of the air passage between the bypass passage and the passage including the air noise removing filter is conducted by means of a two-way valve.

It is also preferred that the switching of the air passage between the bypass passage and the passage including the air noise removing filter is conducted by means of a three-way valve.

BRIEF DESCRIPTION OF THE DRAWINGS

FIGS. 5A, 5B, 5C, 5D, and 5E are partly cut-away v perspective views of different examples of a flow resistor used in the embodiments of the present invention; and FIG. 6 is an illustration of a method for measuring blood pressure.

DESCRIPTION OF THE PREFERRED EMBODIMENTS

Embodiments of the present invention will be described with reference to the accompanying drawings.

Figure 1:
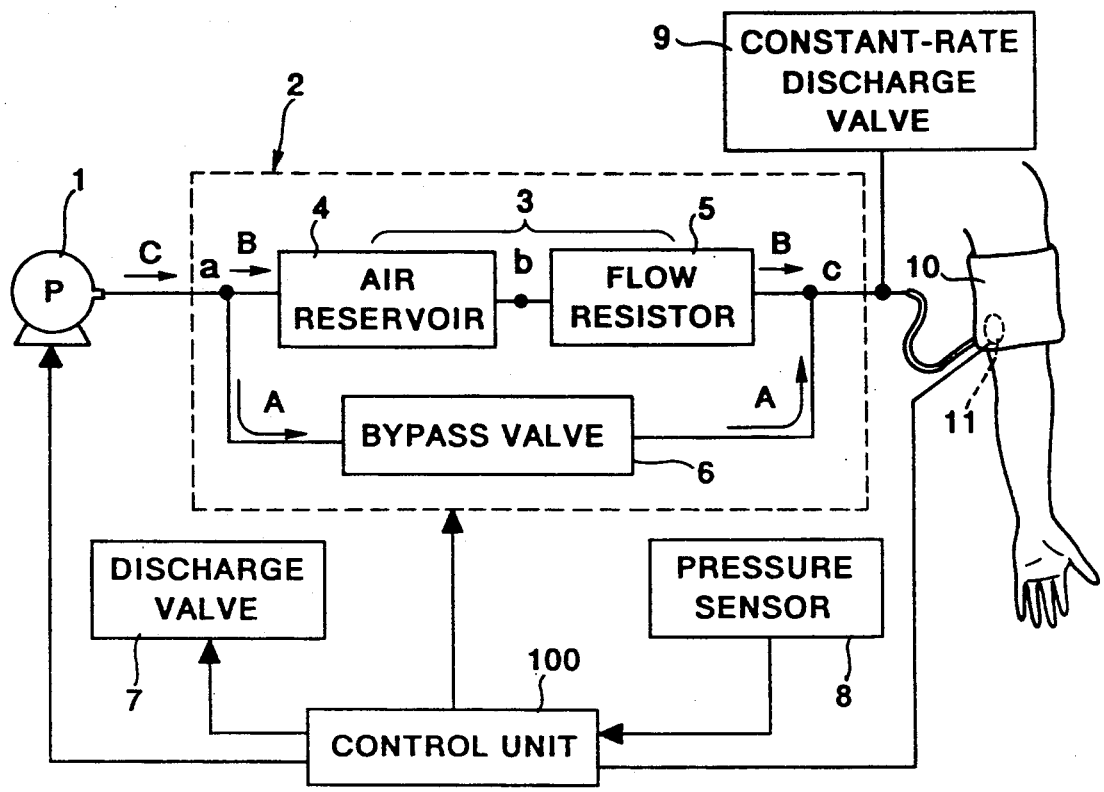
FIG. 1 is a block diagram showing the basic concept of the present invention.

Referring to FIG. 1 showing the basic concept of the present invention, numeral 1 denotes a pressurizing pump, while numeral 2 denotes a pumped air noise removing device used in embodiments of the present invention, the device 2 including an air noise removing device 3 having a series connection of an air reservoir 4 and a flow resistor 5, and a bypass valve 6 which is connected in parallel with the air noise removing filter 3.

A discharge valve 7, a pressure sensor 8 and a constant rate discharge valve 9 are used in controlling the supply and discharge of air to and from the cuff 10. The pressure sensor 8 conducts the control of the state of the bypass valve 6 so as to open and close the bypass passage.

Figure 2A:
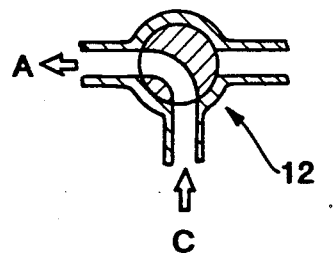
FIG. 2A, FIG. 2B are a sectional view of a three-way air valve.
Figure 2B:
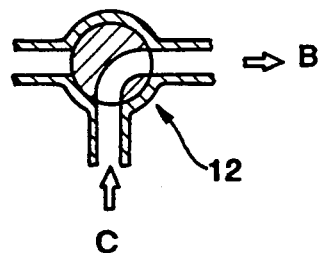

The bypass valve 6 may be substituted by a three-way valve 12 shown in FIG. 2 disposed at one of points a and c shown in FIG. 1, the three-way air valve 12 being capable of receiving air supplied from the pressurizing pump in the direction of an arrow C and then causing the air to flow through the bypass passage as indicated by arrows A. The air pressure generated in the pressurizing pump 1 is introduced into the cuff 10 through the pumped air noise prevention device 2 so that the detection of Korotkoff sound by a microphone 11 embedded in the cuff 10 is conducted without being affected by noise during rising of the pressure in the cuff 10.

When the cuff 10 still has a large dead space or when the cuff pressure is still 20 mmHg or below, air is supplied to the cuff 10 at a large flow rate without eliminating pulsation generated by the pressurizing pump 1 and noises produced by the valves and diaphragm. When the cuff pressure reaching 20 mmHg or completion of charging of the dead space of the cuff is sensed by the pressure sensor 8 so that a control unit 100 produces an instruction for closing the bypass valve 6. In consequence, the air which is pressurized by the pressurizing pump 1 and which contains pulsation and noise is made to flow through the passage having the air noise removing filter 3.

When pulsating air containing noise passes through the air noise removing filter 3 composed of the air reservoir 4 and the flow resistor 5, the air is temporarily accumulated in the air reservoir 4 and then supplied through the flow resistor 5 which serves to restrict the flow of air. Thus, the air pressurized by the pressurizing pump is substantially rectified through the air noise removing filter. Therefore, the detection of the Korotkoff sound by the microphone 11 or detection of the cuff pulsating pressure by the pressure sensor 8 can be conducted with reduced level of noise of the air which is being charged into the cuff. That is, the pumping can be conducted in such a manner as to enable detection of Korotkoff sound during rise of the cuff pressure.

Figure 3:
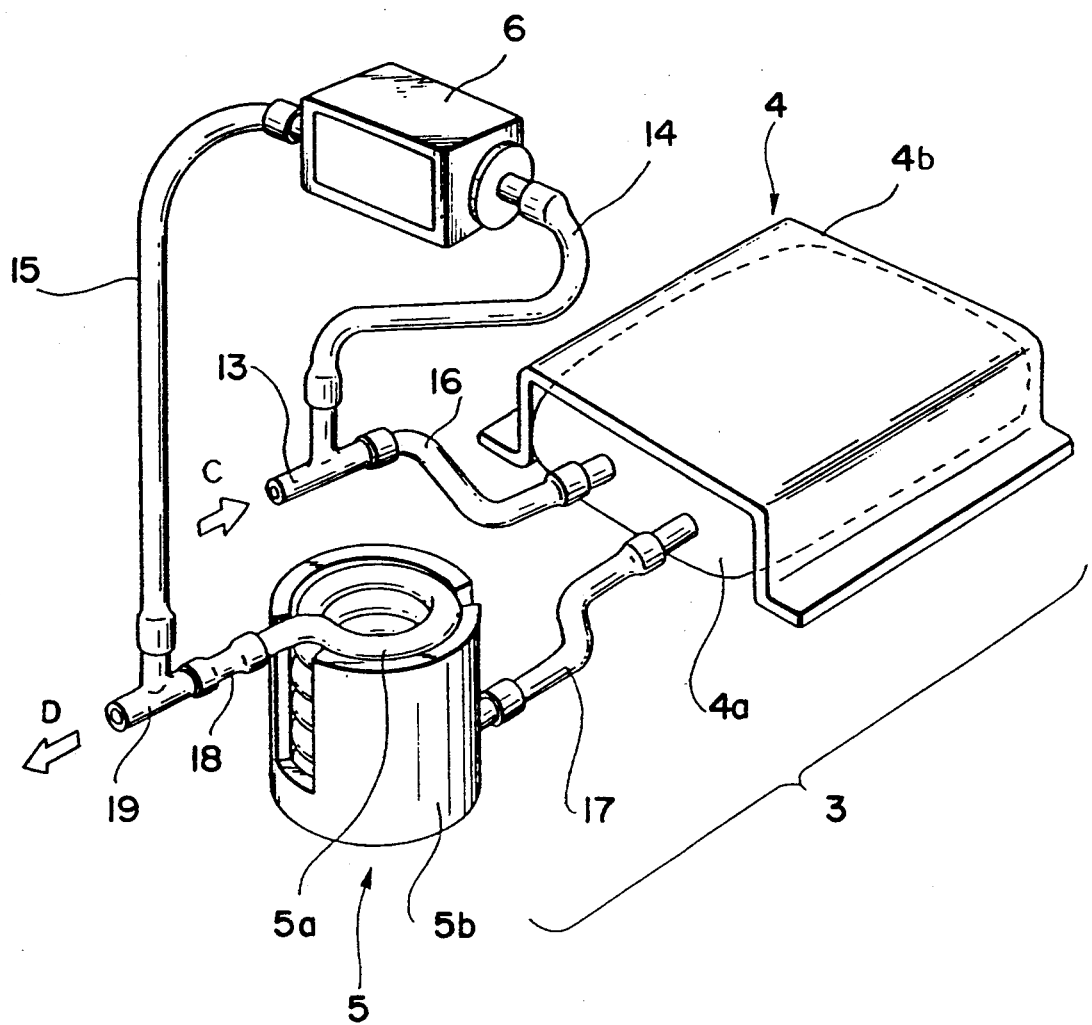
FIG. 3 is a perspective view of an embodiment of the present invention.

FIG. 3 is an illustration of an embodiment of the invention, in particular a pumped air noise removing device which is the portion within a broken-line frame in FIG. 1 showing the basic concept.

The air supplied from the pump 1 as indicated by arrow C is introduced into a T pipe 13 which branches into two lines one of which leads to one end of the bypass valve (two-way air valve) through a pipe 14 while the other is connected to the air reservoir 4a through a pipe 16. In this embodiment, the body 4a of the air reservoir is made of a soft and flexible material such as a rubber, vinyl chloride or the like. A frame 4b which limits the thickness of the air reservoir body 4a prevents the air reservoir body 4a from inflating beyond a predetermined volume. The other end of the bypass valve 6 is connected to a pipe 15 which leads to a T pipe 19.

A pipe 17 is connected to the air reservoir body 4a. The flow resistor 5 has a resistor element 5a which is in this case a tube having an inside diameter of 0.5 to 0.7 mm and a thickness of 1.25 mm. The tube is made of a material which exhibits a small change in diameter and is wound in the form of a coil and placed in a cylindrical housing 5b. The above-mentioned pipe 17 is connected to one end of the resistor element 5a while the other end of the same is connected to the T pipe 19 through a pipe 18.

In the embodiment shown in FIG. 3, when the cuff pressure is still below 20 mmHg, the air from the pump indicated by an arrow C is supplied at a large flow rate directly into the cuff via pipe 15 as indicated by an arrow D because in this state the bypass valve 6 is opened. Then, as the dead space in the cuff is filled with air to raise the internal pressure to 20 mmHg, the bypass valve 6 is closed so that air starts to flow via the pipe 16 so as to pass through the air noise removing filter 3 having an air reservoir 4 and the flow resistor 5.

The air from the pressurizing pump is substantially rectified when flowing through the air noise removing filter 3 and the thus rectified air is supplied to the cuff 10 so as to enable detection of Korotkoff sound or cuff pulsating pressure while the cuff pressure is being increased.

The flow resistor 5 has a resistor element 5a which is coiled and accommodated in the cylindrical housing 5b, while the air reservoir 4 has a reservoir body 4a which is restricted in the thicknesswise direction by the frame 4b. It is therefore possible to make an efficient use of the space or volume inside the body of the sphygmomanometer. For instance, it is possible to obtain a compact and light-weight sphygmomanometer by placing an electronic circuit board of the frame 4b. In addition, the flow resistor can have a long length because the resistor element is coiled. This enables the use of a tube having a comparatively large inside diameter so that pressure loss cross the flow resistor can be diminished.

Figure 4:
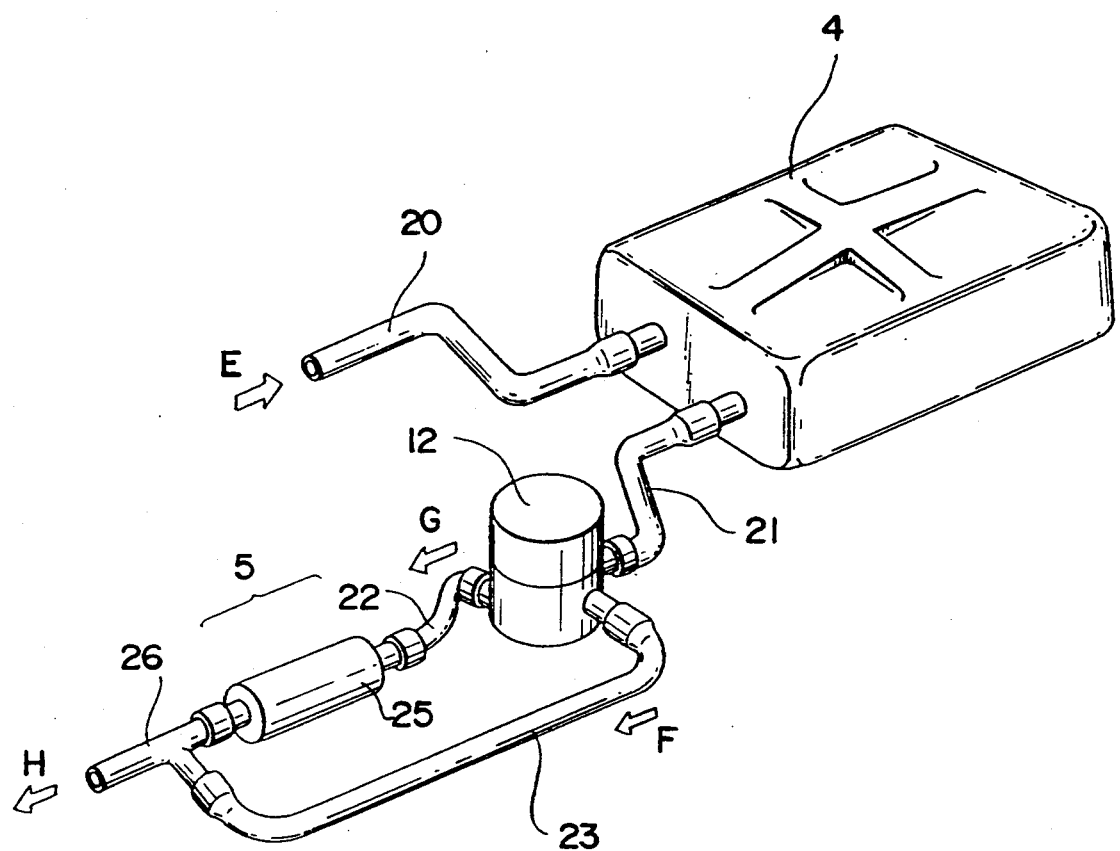
FIG. 4 is a perspective view of another embodiment of the present invention.

FIG. 4 shows another embodiment of the present invention. In this embodiment, a three way air valve 12 shown in FIG. 2 is disposed at the point a or c shown in FIG. 1 showing the basic concept. In addition, the air reservoir 4 is formed of a rigid tank. The flow resistor 5 has a cylindrical housing 25 and a resistor element which is in this case fibers filling the interior of the housing 25.

In this embodiment, the air supplied from the pump in the direction indicated by an arrow E is accumulated in the air reservoir 4 through the pipe 20 and is then introduced to the three-way air valve 12 through a pipe 21.

When the cuff pressure is still 20 mmHg or below, the three-way air valve 12 is so set as to enable air to be directed to the pipe 23 as indicated by an arrow F. The air then flows into the cuff 10 through a T pipe as indicated by an arrow H. When the cuff pressure has reached 20 mmHg, the three-way air valve 12 is switched so as to direct the air in the direction of an arrow G so that the air is introduced through the pipe 22 into the flow resistor 5 which is composed of the cylindrical housing 25.

As a result, the pumped air is made to flow through the air noise removing filter composed of the air reservoir 4 and the flow resistor 5, so that rectified air is supplied into the cuff.

FIGS. 5A to 5E show different examples of the materials used as the resistor element which is charged in the cylindrical housing 25 of the flow resistor 5 used in the embodiment of the invention shown in FIG. 4.

More specifically, FIGS. 5A, 5B, 5C and 5D respectively show fibers 26, tiny beads 27, foamed urethane 28 having continuous pores and non-woven cloth and paper 29, charged in the cylindrical housings 5, respectively.

In the flow resistor shown in FIG. 5E, the cylindrical housing 25 is composed of a pair of parts 25c and 25d which are screwed to each other with an O-ring 30 placed therebetween, the housing 25 being replacably charged with a resistor element made of paper, non-woven cloth 31 or the like material.

The illustrated materials of resistor element have numerous air passages therein and, hence, smaller tendency of clogging with dust or other matters as compared with the flow resistor composed of an orifice having a single restricted opening.

According to this embodiment, the air carrying pulsation generated by the pressurizing pump and noises produced by the valves and diaphragm is supplied to the cuff at large flow rate until the cuff pressure reaches a predetermined level (20 mmHg) and, after this level is reached, the cuff is charged with substantially rectified air. It is therefore possible to detect Korotkoff sound or cuff pulsating pressure with reduced influence of noise, thus making it possible to measure the minimum and maximum blood pressure in the course of rise of the cuff pressure, whereby measurement of blood pressure can be completed in a short time.

In addition, setting of pressure, which is necessary in the sphygmomanometer of the type which measures the blood pressures during gentle fall of the cuff pressure after a rapid rise to the set pressure (maximum blood pressure plus α), can be eliminated. In addition, the precision of measurement of blood pressure can be enhanced by controlling the rate of rise of cuff pressure. Thus, the described embodiment offers a great advantage.

The air noise removing filter which is composed of an air reservoir and a flow resistor can have a compact construction with reduced loss of pressure.

As shown in FIG. 6, the setting of the cuff pressure can be eliminated also in the sphygmomanometer of the type which measures the blood pressure during the fall of the pressure, by roughly measuring the maximum pressure through detection of Korotkoff sound in the course of rise of the cuff pressure and predicting the set level of the cuff pressure high enough to enable measurement.

As will be understood from the foregoing description, according to the present invention, the air having pulsation of the pressure generated by the pressurizing pump and noises produced by valves and diaphragm can be substantially rectified through the air noise removing filter. According to the invention, therefore, it is possible to obtain an automatic sphygmomanometer which can recognize the blood pressure through detection of Korotkoff sound or cuff pulsating pressure in the course of rise of the cuff pressure.

In addition, when the cuff pressure is still below a predetermined level, the automatic sphygmomanometer of the invention enables air to be supplied at a large flow rate through the bypass passage bypassing the air noise removing filter, thus enabling recognition of blood pressure in a short time.

We claim:

1. An automatic sphygmomanometer for recognizing blood pressure through detection of one of Korotkoff sound and pulsation in cuff pressure, comprising:
   a pressurizing pump;
   a cuff;
   an air noise removing filter including an air reservoir and a flow resistor connected in series between said pressurizing pump and said cuff;
   a bypass passage bypassing said air noise removing filter; and
   control means for supplying air, when the cuff pressure is below a predetermined level, from said pressurizing pump into said cuff through said bypass passage to rapidly raise the cuff pressure in said cuff, and, after a predetermined level is reached, supplying the air from said pressurizing pump into said cuff through said air noise removing filter.

2. An automatic sphygmomanometer according to claim 1, wherein said control means includes a pressure sensor producing an output and executes control in accordance with the output from said pressure sensor.

3. An automatic sphygmomanometer according to claim 2, wherein said flow resistor comprises a resistor element made of a porous material.

4. An automatic sphygmomanometer according to claim 2, wherein said flow resistor comprises a resistor element formed by a tube.

5. An automatic sphygmomanometer according to claim 4, wherein said flow resistor further comprises a housing accommodating said tube in a coiled arrangement.

6. An automatic sphygmomanometer according to claim 2, wherein said air reservoir has an outer shell made of flexible material.

7. An automatic sphygmomanometer according to claim 2, wherein said air reservoir comprises:
   a bag made of flexible material; and
   a frame restricting expansion of said bag in at least one direction.

8. An automatic sphygmomanometer according to claim 7,
   wherein said bag has a length, a width and a thickness, the thickness being smaller than both the length and width, and
   wherein said frame restricts expansion of the thickness of said bag.

9. An automatic sphygmomanometer according to claim 1, wherein said control means comprises:
- a two-way air valve connected via said bypass passage to said pressurizing pump and said cuff; and
- means for controlling switching between said bypass passage and said air noise removing filter by said two-way air valve.

10. An automatic sphygmomanometer according to claim 1, wherein said control means comprises:
- a three-way air valve connected via said bypass passage to said pressurizing pump and said cuff; and
- means for controlling switching between said bypass passage and said air noise removing filter by said three-way air valve.

11. An automatic sphygmomanometer according to claim 1, wherein said flow resistor comprises a resistor element made of a porous material.

12. An automatic sphygmomanometer according to claim 1, wherein said flow resistor comprises a resistor element formed by a tube.

13. An automatic sphygmomanometer according to claim 12, wherein said flow resistor further comprises a housing accommodating said tube in a coiled arrangement.

14. An automatic sphygmomanometer according to claim 1, wherein said air reservoir has an outer shell made of flexible material.

15. An automatic sphygmomanometer according to claim 1, wherein said air reservoir comprises:
- a bag made of flexible material; and
- a frame restricting expansion of said bag in at least one direction.

16. An automatic sphygmomanometer according to claim 15,
- wherein said bag has a length, a width and a thickness, the thickness being smaller than both the length and width, and
- wherein said frame restricts expansion of the thickness of said bag.

* * * * *